United States Patent [19]
Edell et al.

[11] Patent Number: 5,411,540
[45] Date of Patent: May 2, 1995

[54] METHOD AND APPARATUS FOR PREFERENTIAL NEURON STIMULATION

[75] Inventors: David J. Edell, Lexington; John L. Wyatt, Jr., Sudbury; Joseph Rizzo, III, Boston, all of Mass.

[73] Assignee: Massachusetts Institute of Technology, Cambridge, Mass.

[21] Appl. No.: 72,320

[22] Filed: Jun. 3, 1993

[51] Int. Cl.$^6$ ............................................. A61N 1/00
[52] U.S. Cl. ......................................... 607/53; 607/2; 607/75; 607/116; 607/54
[58] Field of Search .................... 607/2, 53, 54, 72, 73, 607/74, 75, 76, 115, 116, 118; 600/1, 2, 9

[56] References Cited

U.S. PATENT DOCUMENTS

2,721,316 10/1955 Shaw ..................................... 607/72
5,109,844 5/1992 DeJuan, Jr. et al. .................. 607/53

Primary Examiner—Randall L. Green
Assistant Examiner—P. Zuttarelli
Attorney, Agent, or Firm—Choate, Hall & Stewart

[57] ABSTRACT

The invention provides a method for preferentially stimulating neural somas over neural axons located around the somas but not integral with the somas. In the invention, a positive electrical pulse is applied to a region of neural tissue consisting of one or more neural somas to be stimulated and neural axons, and due to the physiology of the somas, they are preferentially stimulated by the electrical pulse over the neural axons not integral with the somas to be stimulated. The preferential soma stimulation provided by the invention achieves the advantage of locally focusing external stimulation such that it may be directed to particular soma locations for indicating location-dependent sensory information. Thus the pulse scheme of the invention may be employed in prosthetic applications directed to, for example, the retinal ganglia neural tissue.

23 Claims, 2 Drawing Sheets

METHOD AND APPARATUS FOR PREFERENTIAL NEURON STIMULATION

BACKGROUND OF THE INVENTION

This invention relates to techniques for stimulating neural tissue.

The physiology of electrical neuron stimulation is well known. A neuron consists of: a branched pattern of processes, commonly known as dendrites, which act to receive information; a cell body, known as the soma, from which the dendrites extend, and which integrates the received information and provides for the metabolic needs of the neuron; and an axon integral with, i.e., connected to, the soma and extending from the soma, for transporting constituents between the soma and distant synapses, which transfer information to the next set of nerve dendrites.

Neurons may be modelled electrically as distributed capacitors linked by intracellular and extracellular resistances. Neurons are initially, i.e., at a resting time when no stimulation is presented, negatively polarized by about 60 mV–80 mV inside the soma membrane with respect to the outside of the membrane. Depolarization of a soma membrane creates an action potential, which effectively travels via axons to, e.g., the inner brain, thereby sending the stimulation signal to the inner brain. Thus, information is represented in the nervous system as a series of action potentials that travel between the neurons via the membranes of axons. Depolarization of a soma is conventionally achieved by causing current to pass out through a region of the soma membrane. As current flows out of the soma membrane, it acts to largely reduce the polarization potential of the soma, and initiate the soma depolarization, causing an action potential to appear and propagate information along an axon.

In general, outward soma current is typically initiated by transiently forcing the electric potential outside the soma membrane more negative than its resting potential, or conversely by forcing the electric potential inside the soma membrane more positive than its resting potential. In practice, either of these conditions are achieved by flowing current in the appropriate direction through the resistive biological fluids surrounding a neuron.

The outward current flow of depolarization current necessarily causes equivalent inward current flow in another region of the neuron to conserve charge and preserve charge neutrality across the body of the neuron. This independent current largely hyperpolarizes the soma membrane but does not cause an action potential. Neuron stimulation and charge neutrality preservation are thus achieved by manipulation of electrical potentials in the local area of the neuron membrane.

Generally speaking, axons connect neural somas to other somas, as explained above, and thus provide means for delivering electrical information impulses from an exterior neuron to the neurons of the inner brain. Axons pass around many neurons not integral with, i.e., not connected to, those axons in their trajectory from a first neuron to a second neuron at, e.g., the inner brain. As a consequence, external stimulation of a neuron may also unintentionally stimulate an unrelated axon along whose path the neuron is located. Such unintentional axon stimulation results in diffuse, poorly localized neuron activation. This limits the ability to create stimuli indicative of a precise stimuli location in a neural structure.

Figure 1:
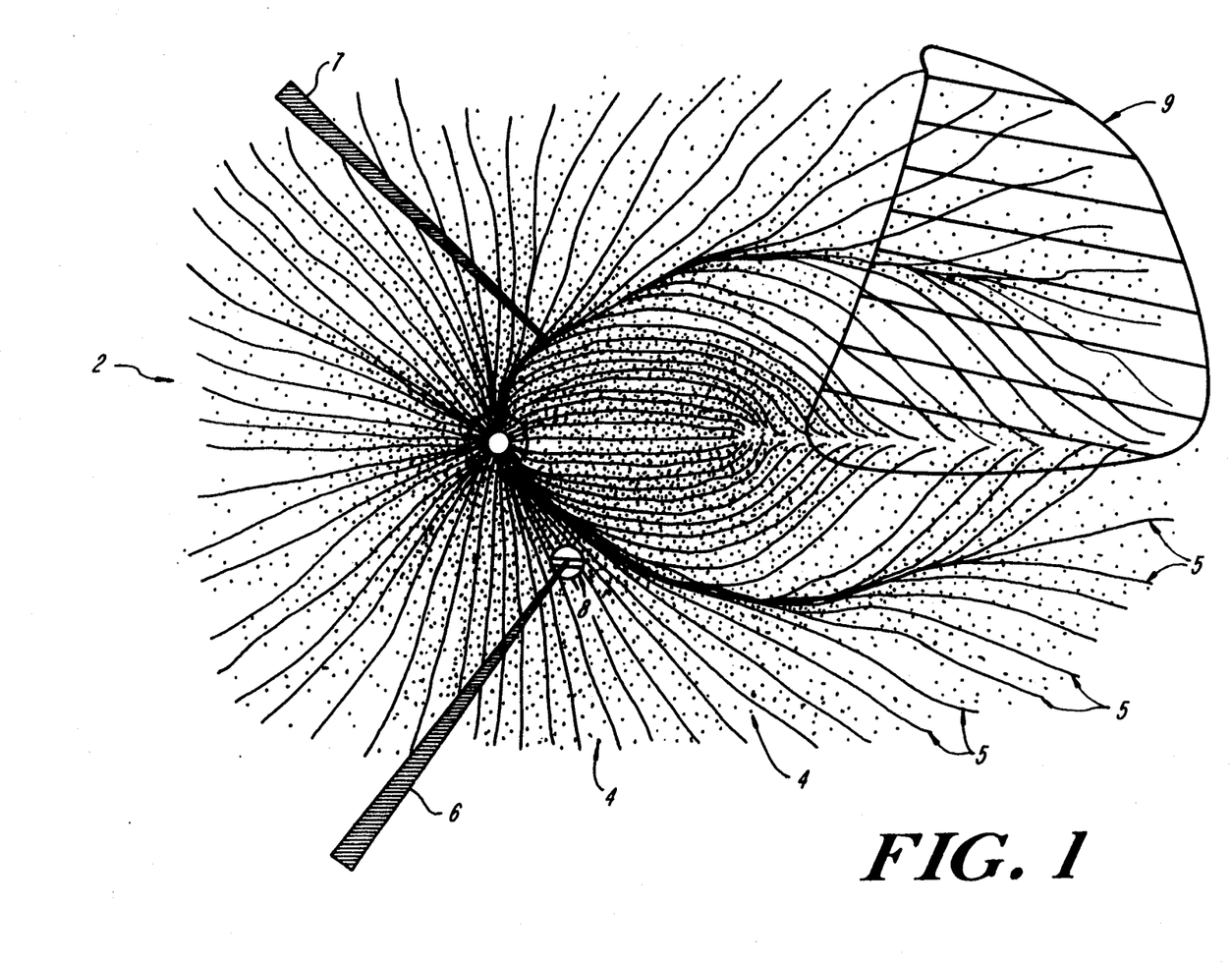
FIG. 1 is a schematic representation of a region of neural retinal tissue.

Referring to FIG. 1, such locally precise stimuli are desirable in, for example, the application of electrical stimuli to retinal ganglia in a visual prosthetic application. FIG. 1 schematically illustrates a region of neural retinal tissue, represented as 2; this tissue includes ganglion somas 4 (tiny dots) and axons 6 (lines). In the case of retinal ganglia stimulation to provide visual signals, stimulus position directly corresponds to visual information encoded in the stimulus. For example, ganglia stimulation with an electrode 6 that, for purposes of discussion, is assumed to ideally focus stimulation, could in theory stimulate a few chosen ganglion somas without stimulating axons around those somas. With this localized stimulation, the brain would then perceive light corresponding to the stimulation to originate at a localized region 8 in the vicinity of the somas. Conversely, ganglia stimulation with an electrode 7 that, for purposes of discussion, is assumed to stimulate a cluster of axons emanating from ganglion somas in a distant region 9 causes an incorrect neural perception of a visual stimulus location at the distant region 9, rather than the intended location at the electrode 7. Stimulation of axons uncorrelated to a neural tissue region of interest is thus seen to provoke unintended, misplaced visual stimulation. Accordingly, the effectiveness of electrical stimulation for retinal prosthetic applications, and indeed any neural stimulation application, is directly impacted by the ability to locally focus neural activations.

SUMMARY OF THE INVENTION

The invention overcomes the limitations of conventional stimulation techniques described above by providing a scheme for focal electrical neuron stimulation such that neuron stimuli are focussed to activate neural somas preferentially over neural axons. This is achieved in the invention by two broad complimentary features of the invention. The first broad feature is the provision of electrical stimuli particularly designed to minimally excite axons around a neural soma of interest that are not integral to the neuron of interest. The second broad feature is the provision of a stimulus electrode particularly designed to locally constrain the lateral extent of applied electrical stimuli to a prespecified neural tissue region, and further to particularly position the spatial orientation of the electric field generated by the stimuli for minimally exciting axons around a soma of interest.

Accordingly, in one aspect, the invention provides a method for preferentially stimulating neural somas over neural axons located around the somas but not integral with the somas. In the invention, a positive electrical pulse is applied to a region of neural tissue consisting of one or more neural somas to be stimulated and neural axons, and due to the physiology of the somas, they are preferentially stimulated by the electrical pulse over the neural axons not integral with the somas to be stimulated. The preferential soma stimulation provided by the invention achieves the advantage of locally focusing external stimulation such that it may be directed to particular soma locations for indicating location-dependent sensory information. Thus the pulse scheme of the invention may be directed to, for example, the retinal ganglia neural tissue.

Preferably, the applied electrical pulse of the invention comprises a pulse of a duration between about 1 $\mu$sec and 500 $\mu$sec, and more preferably of a duration between about 20 $\mu$sec and 200 $\mu$sec. The applied electrical pulse comprises a pulse amplitude of between about 0.1 µA and 500 µA, and more preferably between about 1 µA and 100 µA. The positive pulse preferably comprises a train of pulses of a frequency between 0 and about 1 KHz.

In another aspect, the invention provides for positioning a stimulating electrode adjacent to the region of neural tissue containing the somas to be stimulated. In preferred embodiments, the stimulating electrode consists of a first, inner disk-shaped conducting region surrounded by a second annular conducting region, the first and second conducting regions being separated by an insulating region. The inner disk-shaped conducting region in preferred embodiments has a diameter of about 10 µm, and the second annular conducting region has a diameter of about 25 µm and a radial width of about 3 µm. Preferably, the first and second conducting regions each comprise iridium oxide, and the insulating region comprises silicon nitride.

In another aspect, the invention provides a method for preferentially stimulating neural somas over neural axons not integral with the somas by applying to a region of neural tissue including the somas and axons an electrical pulse that produces an electric field in the tissue oriented to preferentially stimulate the somas over the axons not integral with the somas to be stimulated.

In preferred embodiments, the electrical pulse results in depolarization of axons integral with the somas to be stimulated. In other preferred embodiments, the electrode consists of a first rectangular conducting region and a second rectangular conducting region, the two conducting regions being separated by an insulating region and aligned such that a longest side of the first conducting region is parallel to a longest side of the second conducting region. Preferably, the first and second conducting regions are positioned on the neural tissue to be stimulated such that the longest side of each of the first and second conducting regions is oriented parallel to a longitudinal axis of axons within the tissue. In other preferred embodiments, the first and second conducting regions are positioned on the neural tissue to be stimulated such that said longest side of each of the first and second conducting regions is oriented perpendicular to a longitudinal axis of axons within the tissue.

Further features and advantages of the invention will be apparent from the claims which follow and from the following description of a preferred embodiment of the invention.

DESCRIPTION OF A PREFERRED EMBODIMENTS

The features of the neural stimulation scheme of the invention will be described in connection with a retinal prostheses application for clarity in understanding the particular advantages of the invention, but it is intended that the invention not be limited to this one application.

Retinal prostheses could be based on a scheme of stimulating action potentials in ganglion cells of the retina; the action potentials are particularly generated to correspond to a focal visual image area. In one such approach, small metallic electrodes are placed in dose proximity to the ganglion cell bodies, and electrical current is passed through the electrodes. The flow of electrical current creates potential gradients in the vicinity of the neurons of interest. These potential gradients in turn cause potential differences to appear across the soma membranes. Depending on the polarity of the applied potential gradient, the resulting capacitive charging of the membrane causes current to flow in one corresponding direction across the membrane, in the local area near to the electrode, but in the opposite direction across the membrane at an area distant from the electrode. At the local area where current flows out of the soma, the membrane is depolarized (takes on a less negative potential difference), resulting in activation of the membrane changes required to initiate and propagate an action potential.

At the local area where current flows into the soma, the membrane becomes hyperpolarized (takes on a more negative potential difference). This hyperpolarization causes no effect. However, if the degree of hyperpolarization is sufficient, the relaxation of charge which occurs when the electrical stimulus is removed can cause enough current to flow out of the soma to create a depolarization event sufficient to initiate an action potential. This type of action potential initiation is known as anodal break excitation.

Typically, by focusing current to a localized area, selective activation of a limited number of neurons can be achieved. However, the inventors herein have recognized that, in the case of cortical or retinal stimulation, and indeed for neural stimulation in general, an additional neural activation focus mechanism is required to predictively activate somas preferentially over axons which pass around the somas. The conventional stimulation technique of applying stimulation currents to localized tissue regions of interest, while minimizing the extent of the stimulating field on a macro-scale, does not by itself provide for selective stimulation of somas over axons, as discussed above in connection with FIG. 1.

Considering the effect of particular stimulation waveforms on stimulation selectivity, conventional stimulation waveforms, as discussed above, for stimulating a neuron in general, are negative current pulses designed to lower the potential outside an excitable nerve membrane, resulting in outward current flow through the membrane, as discussed above. This outward current flow results in depolarization of the membrane and initiation of an action potential. Such a stimulation scheme is effective only if there exist sufficient sodium channels in the local stimulation area of the membrane to be depolarized, and additionally only if the depolarization excitation is provided for a time sufficient to relax the membrane capacitance, based on the plasma time constant of the membrane.

In particular, in the case of neural soma and axon stimulation, axons are typically easily stimulated by negative currents, thereby causing negative extracellular excursions, because a local area of the axon can be depolarized by outward current flow. Further, loop currents can flow into the axon in a distributed manner with minimal resistance. Because the membrane area of an axon is small, relative to a soma, and because the axoplasm resistance is equivalent to one-half the axon resistance in each direction, the activation time constant for an axon is also small, relative to a soma.

Positive currents are generally not chosen for direct neural axon stimulation because positive currents locally hyperpolarize the membrane of the body being excited and only depolarize the membrane in a distributed manner at a location distant to the electrode. In this case, because the current coupled into a membrane is limited to a small hyperpolarized region, the distributed current flowing out of the membrane has a lower current density than that flowing into the membrane. Proportionally more current, and hence a greater extracellular potential, is thus needed to couple current into the membrane to provide distributed outward current sufficient to depolarize the axon above the threshold for activation potential initiation. Accordingly, the lowest stimulation thresholds for axons are achieved using negative stimulation currents.

The inventors herein have recognized that electrical stimulation of a soma is fundamentally different than stimulation of an axon, and thus, the considerations discussed above do not necessarily apply to soma excitation. The reasoning for this conclusion is as follows. Considering first a negative stimulation pulse, if a negative current pulse is produced by a microelectrode in close proximity to a soma, current flows out of the soma to the region of lower potential. To supply this outward current flow, positive charge can flow into the corresponding axon hillock and nearby regions of the axon in a distributed fashion, hyperpolarizing the axon hillock membrane and nearby regions. Two factors make this scheme unfavorable for soma stimulation. First, there are few sodium channels on a typical soma membrane, and as explained above, stimulation is difficult or impossible for a membrane having few sodium channels. Additionally, an axon represents a large resistance in series with the large soma membrane capacitance, and thus acts to slow the depolarization of the membrane capacitance, thereby requiring a longer excitation time period.

Considering each of these factors in more detail, a minimum number of sodium channels must be open in a membrane being excited for an action potential current to flow and initiate an action potential. It is the inward flow of sodium current that causes this equivalent flow of current out of the membrane to propagate the intended action potential. The existence of few sodium channels in a given soma thereby indirectly indicates that the membrane, when triggered, may not have sufficient ability to allow sodium to cross the cell membrane for initiating an action potential in the axon of that cell.

Even if sufficient sodium channels exist, the large series resistance presented by the axon provides a series element such that the potential difference generated by the waveform stimulus drops across the axon rather than the soma, as intended, unless either the stimulus duration or amplitude is increased. Thus, given these considerations, soma are more difficult to stimulate with negative pulses than are axons.

The inventors herein have recognized that, in contrast to this, positive waveform pulses, while requiring higher stimulus intensities for axons, require lower stimulus intensities for somas, due to the physiological geometry of neural axons. This is because the membrane activation for positive pulses is at a location distant to the local area near to the stimulating electrode, as explained above. Current from a positive pulse flows easily into a soma through the large surface area of the soma membrane, thereby hyperpolarizing the soma membrane in the region of the electrode. This current flows into the cell's axon hillock and axon, as explained above, and then flows out of the axon, at a point distant from the potential field generated by the stimulation electrode, where depolarization of the axon membrane accordingly results.

In addition to this distinction in soma and axon stimulation, the required stimulation threshold for somas is much lower than for axons because of the large soma membrane area available for coupling current into the cell. Further, a cell can easily provide the required sufficient outward current density through the smaller area of the corresponding axon membrane, perhaps at the axon hillock where currents are thought to summate. Conversely, the required stimulation threshold for axons is higher than for cells because the corresponding membrane area available for coupling charge into a soma is small for an axon, and current must flow bidirectionally along an axon and out of the axon in a distributed manner over a relatively large surface area.

Figure 2:
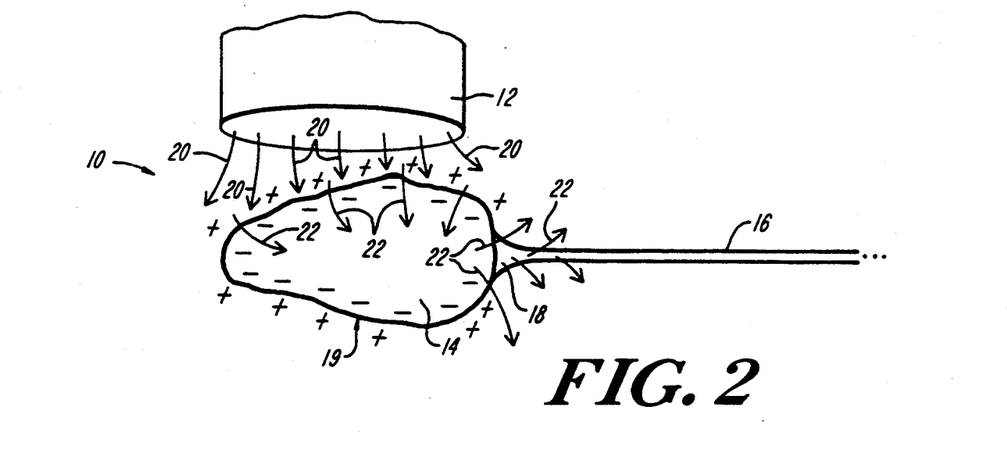
FIG. 2 is a schematic representation of a neural stimulation pulse scheme according to the invention.

Referring to FIG. 2, the inventors herein have recognized that based on the physiological considerations discussed above, selective activation of neural somas over axons is efficiently achieved using a stimulation scheme comprising positive current pulses, this positive stimulation scheme 10 of the invention being shown in FIG. 2. In this scheme, an electrode 12, shown schematically in the figure, is located in close proximity to a soma 14 to be stimulated. The soma 14 is shown with its corresponding axon 16, connected at the axon hillock 18. The soma is shown at a resting state in which the soma membrane 19 is polarized with the inside of the membrane biased negative with respect to the outside of the membrane, as indicated by the plus (+) and minus (−) signs in the figure. Application of positive current pulses 20 to the soma 14 via the electrode causes hyperpolarization of the soma in the region of the electrode, and outward current flow 22 at the axon 16 and axon hillock 18. This outward current 22 depolarizes the membrane at that location and initiates an action potential from the soma through the axon 16, as desired, with minimal, if any excitation of other axons (not shown) unrelated to that cell including the soma 14 and axon 16 of interest. The unrelated (not integral) axons are not stimulated for the reasons explained above. As discussed in connection with FIG. 1, these unrelated axons are physically located around the vicinity of the soma of interest, and may be considered as residing within a region of neural tissue that is effected by the electric field generated by the applied electrical stimulus.

A positive pulse scheme according to the invention for stimulating retinal ganglia somas over axons, for example, comprises a waveform pulse of a duration between about 1 $\mu$sec and about 500 $\mu$sec; and is between about 20 $\mu$sec and about 200 $\mu$sec, preferably. Such a retinal stimulation pulse is of an amplitude of between about 0.1 $\mu$A and about 500 $\mu$A; and is between about 1 $\mu$A and about 100 $\mu$A, preferably. Given these duration and amplitude ranges, the retinal stimulation pulse is of a charge of between about 0.1 pC and about 2.5 nC; and is between about 20 pC and about 20 nC, preferably. A train of such stimulation pulses should generate a stimulation pattern which matches the natural frequency with which the neural somas would generate action potentials. Accordingly, the pulse scheme should be provided with an operating frequency range of at least up to 1 KHz.

The inventors herein have additionally recognized that the particular geometry of an electrode used to deliver the soma stimulation pulses of the invention has a direct impact on the effectiveness of the stimulation pulses. A large electrode or a planar electrode array may supply an amount of current sufficient to stimulate both the cell body and surrounding axons, thereby negating the effective difference in stimulation threshold relied on, as explained above.

Figure 3:
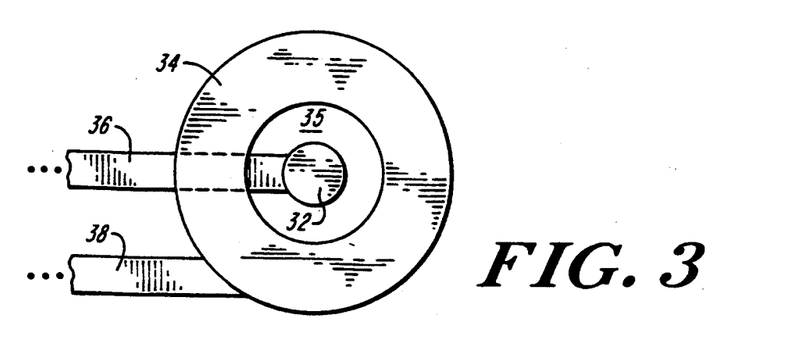
FIG. 3 is a planar view of one electrode according to the invention for delivering the pulse scheme of FIG. 2.

Referring to FIG. 3, local lateral constraint of neuron stimulation current is achieved using an electrode according to the invention, one embodiment of which is shown in FIG. 3. In this scheme, the stimulation electrode comprises a concentric ring structure 30 given schematically in FIG. 3. The ring electrode 30 consists of an inner circular conducting region 32, and an outer annular conducting region 34 surrounding the circular region, the two conducting regions being electrically isolated by a separating insulating region 35. Stimulating pulses (see FIG. 2) are delivered through the central circular conductor 32 and the annular conductor 34 provides a current return ring. Conducting leads 36, 38 provide connection to the central conductor 32 and the annular ring 34, respectively. With this design, the stimulation electrode constrains the lateral divergence of current in the neural tissue to a local area defined by the annular ring, and minimizes the number of somas activated by a particular electrode. Perhaps more importantly, use of the appropriate stimulation waveform according to the invention with the electrode limits the number and area of axon membranes that may undergo depolarization stimulation. Due to the electrode geometry, discussed in detail below, the current density provided by the electrode is highest under the central stimulating conductor 32. Accordingly, the potential difference applied by the stimulation is also the greatest at this point, resulting in enhanced current flow into the membrane under the central stimulating electrode, but not under the return electrode ring 34.

Considering the geometry of the stimulation electrode 30 in more detail, the diameter of the inner circular, disk-shaped conductor 32 may be between, e.g., 1 $\mu$m–500 $\mu$m, depending on the proximity of the electrode structure to the neural tissue, the size of the neural somas to be stimulated, and the ultimate electrical threshold requirement for current, and thus charge, to pass through the electrode without damage to the electrode, or the production of electrochemical byproducts. The farther the electrode is spaced from the neural tissue surface, the larger the charge and corresponding electrode size requirement. Ideally, the electrode should be large enough to cover a soma of interest and some of the corresponding nerve dendrites. The outer return ring 34 should be spaced as close to the inner disk-shaped conductor 32 as is consistent with the spacing from the electrode to the neural tissue surface. If the electrode is positioned closely to the neural surface, then the electrode conductor spacing should be close to minimize axon activation. On the other hand, if the electrode is positioned farther from the neural surface, then the space between the circular and annular conductors should be correspondingly larger to allow enough potential to develop between the conductors for stimulating the soma under the electrode. Because the current returning into the ring conductor causes potential excursions near the conductor which may excite nearby axons, the annular return ring area should be large, thereby minimizing the current density returning through that conductor and hence minimizing the potential excursion in the area of the conductor. Accordingly, the return ring conductor's geometric surface should be about 2–10 times the area of the inner circular conductor area. Additionally, the outer ring diameter should be of a size consistent with the size of somas to be stimulated. For example, for a total electrode diameter of 25 $\mu$m, corresponding to the approximate diameter of a ganglion soma, the outer ring diameter is, of course, also 25 $\mu$m, the inner circular conductor is 10 $\mu$m in diameter, and the outer ring is about 3 $\mu$m-wide.

Figure 4:
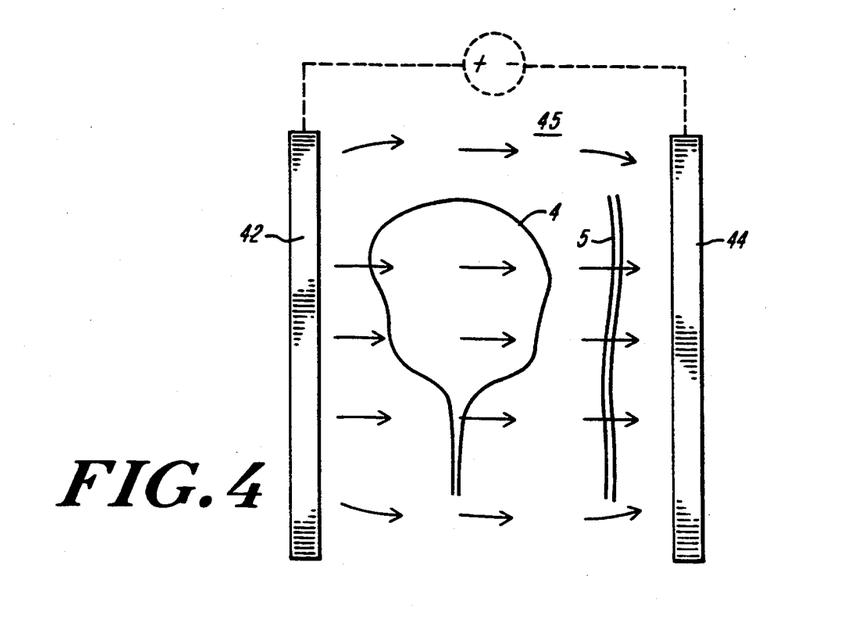
FIG. 4 is a planar view of a second electrode according to the invention for delivering the pulse scheme of FIG. 2.

Referring now to FIG. 4, a second embodiment of an electrode structure according to the invention is based on the physical geometrical differences between neural somas and axons. Ganglion somas, for example, are generally approximately spherically symmetrical in shape, while axons are generally shaped like long, thin wires of about 1 micron in diameter and up to several millimeters in length in the retina, for example. Axons run nearly parallel to one another in the local regions of the retina, as shown in FIG. 1, and the angular orientations of the axons in each region of the retina are well known. Exploiting this soma-axon geometric distinction, an electrode 40 according to the invention is designed to produce an electric field that selectively stimulates ganglion somas more easily than axons.

Considering an axon as a cylindrical structure, it is known that electric fields directed radially, i.e., perpendicular to the axis of the axon cylinder, do not readily stimulate axons, while electric fields directed axially, i.e. parallel to the axis of the axon cylinder, more easily stimulate axons. Based on this physiological consideration, one electrode according to the invention provides an electrode geometry which when oriented correctly in relation to the orientation of axons beneath the electrode, produces an electric field that primarily runs perpendicular to the axon axis, and accordingly does not tend to stimulate those axons. While one embodiment of the electrode according to the invention is described here, it is intended that the invention encompass, in general, any electrode geometry for which an electric field is generated to preferentially stimulate a neural soma over axons around that soma.

As shown in FIG. 4, such an electrode consists of two parallel conductors 42, 44 laterally separated by an insulating region 45. Conducting leads 46, 48 provide for electrical connection to the conductors 42, 44, respectively. In use, the pair of conductors is oriented on neural tissue to be stimulated in such a way that the path of electric field lines from one conductor 42 to the other 44 is perpendicular to the longitudinal axis of axons around the electrode. This orientation tends to produce electric fields that thereby stimulate somas rather than axons. Alternatively, the electrode may consist of two adjacent wires, oriented parallel to each other, and positioned orthogonal to the longitudinal axis of axons located in the vicinity of the electrode.

Considering the geometry of this electrode in more detail, each electrical conductor 42, 44 of the pair is of a width of between about 1 $\mu$m and about 100 $\mu$m; and nominally is between about 4 $\mu$m and about 20 $\mu$m-wide. The length of each conductor 42, 44 is between about 3 $\mu$m and about 500 $\mu$m; and nominally is between about 10 $\mu$m and about 80 $\mu$m-long. The insulating space between the two conductors is of a width between about 1 μm and about 600 μm; and nominally is between about 5 μm and about 40 μm-wide.

Considering choices for stimulation electrode material, independent of electrode geometry, to avoid electrochemical reactions, any electrode structure according to the invention should comprise, e.g., an inert material such as iridium, iridium oxide, platinum, rhodium, or other nobel metal. Iridium oxide is preferred, but depending on the electrode size and spacing to the neural tissue, other nobel metals or other materials may be of choice. Using iridium oxide as a conductor material, silicon nitride is preferred as an insulating material, but like the selection of conductor material, other insulators may be of choice for a particular electrode application.

Electrodes according to the invention may be provided on a support structure like that taught in copending U.S. patent application Ser. No. 07/943,513, entitled "Low-pressure Neural Contact Structure," filed on Sep. 11, 1992, in the names of Edell et al., which application is hereby incorporated by reference. In such a support scheme, specifically designed for the retinal environment, an electrode or array of electrodes is held in contact with the neural tissue surface of the retina with a flexible support member for stimulation of retina ganglia. Alternatively, any suitable support structure for positioning the electrode of the invention in the vicinity of neural tissue of interest to deliver the stimulation pulses of the invention to such tissue is contemplated by this invention.

Accordingly, the pulse stimulation scheme and electrode design of the invention is applicable to a wide range of stimulation prosthetics for visual, auditory, or other sensory systems. For example, in addition to stimulation of neurons related to vision, the stimulation and electrode scheme may be used for functional electrical stimulation of spinal cord neurons, ganglia for bladder activation, dorsal root ganglion neurons, and autonomic nerves such as the vagal nerve, for treating epilepsy, or activation of paretic limbs, or in treatment for impotence. The stimulation pulse scheme and electrode design of the invention is thus intended to be applied to any neural tissue for preferential stimulation of neural somas over axons in that tissue, and is not limited to a particular neural application.

We claim:

1. A method for preferentially stimulating neural somas with respect to neural axons located near the somas but not integral with the neural somas, in a region of neural tissue comprising: positioning a stimulating electrode in the vicinity of the region of neural tissue and, applying a positive electrical pulse to the region of neural tissue including one or more neural somas to be stimulated and neural axons to lower a stimulation thresholds of the neural somas with respect to thresholds of the non-integral neural axons, whereby the neural somas of the neural tissue are preferentially stimulated by the positive electrical pulse over the neural axons not integral with the neural somas to be stimulated.

2. The method of claim 1 wherein the step of applying a positive electrical pulse comprises applying a positive electrical pulse of a duration between about 1 μsec and about 500 μsec.

3. The method of claim 2 wherein the step of applying a positive electrical pulse comprises applying a positive electrical pulse of a duration between about 20 μsec and about 200 μsec.

4. The method of claim 2 wherein the step of applying a positive electrical pulse comprises applying a positive electrical pulse of an amplitude between about 0.1 μA and about 500 μA.

5. The method of claim 4 wherein the step of applying a positive electrical pulse comprises applying a positive electrical pulse of an amplitude between about 1 μA and about 100 μA.

6. The method of claim 1 wherein the step of applying a positive electrical pulse comprises applying a train of pulses.

7. The method of claim 6 wherein the step of applying a train of pulses comprises applying a train of pulses, each pulse of the train of pulses being of a duration between about 1 μsec and about 500 μsec.

8. The method of claim 7 wherein the step of applying a train of pulses comprises applying a train of pulses at a frequency of between 0 KHz and about 1 KHz.

9. The method of claim 1 wherein said region of neural tissue comprises retinai ganglia neural tissue.

10. The method of claim 9 wherein the step of applying a positive electrical pulse comprises applying a train of pulses.

11. The method of claim 10 wherein the step of applying a train of pulses comprises applying a train of pulses, each pulse of the train of pulses being of a duration between about 1 μsec and about 500 μsec.

12. The method of claim 11 wherein the step of applying a train of pulses comprises applying a train of pulses at a frequency of between 0 KHz and about 1 KHz.

13. The method of claim 1 wherein the step of positioning a stimulating electrode comprises positioning a stimulating electrode comprising of a first, inner disk-shaped conducting region surrounded by a second annular conducting region, the first and second conducting regions being separated by an insulating region.

14. The method of claim 13 wherein the step of positioning a stimulating electrode comprises positioning a stimulating electrode comprising of a first, inner disk-shaped conducting region having a diameter of about 10 μm, surrounded by a second annular conducting region having a diameter of about 25 μm and a radial width of about 3 μm.

15. The method of claim 13 wherein the step of positioning a stimulating electrode comprises positioning a stimulating electrode comprising of first and second conducting regions each comprising iridium oxide, the first and second conducting regions being separated by an insulating region comprising silicon nitride.

16. The method of claim 13 wherein the step of positioning a stimulating electrode comprises positioning a stimulating electrode comprising of a first, inner disk-shaped conducting region surrounded by a second annular conducting region, the second annular conducting region comprising a lateral area of between about 2 and about 10 times a lateral area defined by the disk-shaped conducting region.

17. A method for preferentially stimulating neural somas with respect to neural axons located near the somas but not integral with the somas, in a region of neural tissue comprising: positioning a stimulating electrode in the vicinity of the region of neural tissue and, of applying an electrical pulse to the region of neural tissue including one or more neural somas to be stimulated and neural axons to lower stimulation threshold of the neural somas with respect to thresholds of the non-integral neural axons, the electrical pulse producing an electric field in the neural tissue oriented to preferentially stimulate the neural somas over the neural axons not integral with the somas to be stimulated to initiate an action potential.

18. The method of claim 17 wherein the step of applying an electrical pulse comprises applying an electrical pulse to depolarize axons integral with the somas to be stimulated.

19. The method of claim 17 wherein said region of neural tissue comprises retinal ganglia neural tissue.

20. The method of claim 17 wherein the step of positioning a stimulating electrode comprises positioning a stimulating electrode comprising of a first rectangular conducting region and a second rectangular conducting region, the two conducting regions being separated by an insulating region and aligned such that a longest side of the first conducting region is parallel to a longest side of the second conducting region.

21. The method of claim 20 wherein the step of positioning a stimulating electrode comprises positioning said first and second conducting regions on said neural tissue such that said longest side of each of the first and second conducting regions is oriented perpendicular to a longitudinal axis of said axons.

22. The method of claim 20 wherein the step of positioning a stimulating electrode comprises positioning said first and second conducting regions on said neural tissue such that said longest side of each of the first and second conducting regions is oriented parallel to a longitudinal axis of said axons.

23. The method of claim 20 wherein the step of positioning a stimulating electrode comprises positioning said first and second conducting regions, each comprising iridium oxide, the two conducting regions being separated by an insulating region comprising silicon nitride.

* * * * *

UNITED STATES PATENT AND TRADEMARK OFFICE
CERTIFICATE OF CORRECTION

PATENT NO. : 5,411,540

DATED : May 2, 1995

INVENTOR(S) : David J. Edell, John L. Wyatt, Jr. and Joseph Rizzo, III

It is certified that error appears in the above-indentified patent and that said Letters Patent is hereby corrected as shown below:

Column 2, line 13: please delete "to ideally focus" and insert therefor -- ideally to focus --;

Column 2, line 30: please delete "to locally focus" and insert therefor -- locally to focus --;

Column 2, line 36: please delete "focussed" and insert therefor -- focused --;

Column 2, lines 40-41: please delete "to minimally excite" and insert therefor -- to excite minimally --;

Column 2, line 44: please delete "to locally constrain" and insert therefor -- to constrain locally --;

Column 2, line 46: please delete "to particularly position" and insert therefor -- to position particularly --;

Column 4, line 7: please delete "dose" and insert therefor -- close --;

Column 4, line 57: please delete "exist" and insert therefor -- exists --;

Column 6, line 52: please delete "effected" and insert therefor -- affected --;

Column 8, line 45: please delete "to preferentially stimulate" and insert therefor -- preferentially to stimulate --;

UNITED STATES PATENT AND TRADEMARK OFFICE
CERTIFICATE OF CORRECTION

PATENT NO. : 5,411,540

DATED : May 2, 1995

INVENTOR(S) : David J. Edell, John L. Wyatt, Jr. and Joseph Rizzo, III

It is certified that error appears in the above-indentified patent and that said Letters Patent is hereby corrected as shown below:

Column 9, line 54: Please delete "a";

Column 9, line 60: after "stimulate" please insert -- to initiate an action potential. --;

Column 10, line 20: please delete "retinai" and insert therefor -- retinal --;

Column 10, lines 33, 39, 46 and 52: after "comprising" please delete "of";

Column 10, line 62: after "and" please delete "of";

Column 10, line 65: please delete "threshold" and insert therefor --thresholds --; and Column 11, line 12: after "comprising" please delete "of".

Signed and Sealed this

Fourteenth Day of November, 1995

Attest:

BRUCE LEHMAN

*Attesting Officer*         *Commissioner of Patents and Trademarks*